United States Patent [19]

Medero et al.

[11] Patent Number: 4,543,962
[45] Date of Patent: Oct. 1, 1985

[54] METHOD OF AUTOMATED BLOOD PRESSURE DETECTION

[75] Inventors: Richard Medero, Lutz; Rush W. Hood, Tampa; Howard P. Apple, Tampa; Maynard Ramsey, III, Tampa, all of Fla.

[73] Assignee: Critikon, Inc., Tampa, Fla.

[21] Appl. No.: 628,861

[22] Filed: Jul. 9, 1984

[51] Int. Cl.⁴ .............................................. A61B 5/02
[52] U.S. Cl. ..................................... 128/682; 128/680
[58] Field of Search ................. 128/672, 677, 680–683

[56] References Cited

U.S. PATENT DOCUMENTS 4,349,034  9/1982  Ramsey, III ........................ 128/681
4,360,029 11/1982  Ramsey, III ........................ 128/681
4,461,266  7/1984  Hood, Jr. et al. ................... 128/681

OTHER PUBLICATIONS

Looney, Jr., "Blood Pressure by Oscillometry"; Med. Electr., 4-1978, pp. 57-63.
Link, "Automatic Electronic Blood Pressure Monitor Using Waveform Analysis Oscillometry"; Norse Systems, Inc. 11-1974.

Primary Examiner—Lee S. Cohen
Assistant Examiner—Angela D. Sykes
Attorney, Agent, or Firm—Audley A. Ciamporcero, Jr.

[57] ABSTRACT

A pressure cuff on the patient is inflated to a predetermined pressure above systolic, and then is deflated incrementally. At each decrement, oscillatory complexes are detected, and respective peaks are compared and evaluated as "true" complexes if they are within certain size matching criteria. After such "true" complexes are identified at a predetermined number of levels (e.g. 2 or 3), only a single complex is investigated at subsequent levels, provided specified size and timing criteria are met.

4 Claims, 3 Drawing Figures

METHOD OF AUTOMATED BLOOD PRESSURE DETECTION

FIELD OF THE INVENTION

This invention relates to automated blood pressure monitors employing the oscillometric method of detection, and more particularly to artifact rejection and analysis methods which improve the overall timing response of the unit.

BACKGROUND OF THE INVENTION

The oscillometric technique for blood pressure measurement was developed long ago, but has only found extensive utility more recently, with the advent of inexpensive integrated circuits and even less expensive microprocessor controlled automated blood pressure monitoring systems. Thus, while indirect, manual oscillometric measurement is described in The Southwestern Veterinarian, Vol. 23, Summer of 1970, No. 4, pp. 289-294, practical oscillometry tends to be found in numerous commercial systems wherein a dedicated microprocessor with stored program control operates by controlling cuff pressure, sensing pressure fluctuations caused by heart beats, and performing the requisite calculations which yield heart rate, mean arterial pressure, and systolic and diastolic pressures. The advent of very large-scale integration portends a change from software systems back to hard wired systems, wherein an entire specially configured machine circuit may be included on but a single chip, but in all events such increasing sophistication and decreasing cost provides further supports for the increasing popularity of automated blood pressure monitors.

Of particular interest with respect to the principles of the present invention are the concepts set forth in U.S. Pat. Nos. 4,360,029 and 4,394,034 to M. Ramsey, III, which are commonly assigned with the instant invention. The Ramsey patents derive from common parentage, the former including apparatus claims and the latter including method claims, their division having been made in response to a restriction requirement during the prosecution. Both patents, however, carry common disclosures of apparatus and methods for artifact rejection in oscillometric systems, which have been in practice in the commercially successful DINAMAP* brand monitors, which are manufactured and marketed by Critikon, Inc., of Tampa, FL, the assignee hereof. In accordance with the Ramsey patents, an inflatable cuff is suitably located on the limb of a patient, and is pumped up to a predetermined pressure. Thereupon, the cuff pressure is reduced in predetermined decrements, at each level of which pressure fluctuations are monitored. These typically consist of a DC voltage with a small superimposed variational component caused by arterial blood pressure pulsations (referred to herein as "oscillatory complexes"). Therefore, after suitable filtering to reject the DC component and to provide amplification, pulse peak amplitudes above a given baseline are measured and stored. As the decrementing continues, the peak amplitudes will normally increase from a lower amount to a relative maximum, and thereafter will decrease. The lowest cuff pressure at which the oscillations have a maximum peak value is representative of mean arterial pressure. Systolic and diastolic pressures may be evaluated either as predetermined fractions of mean arterial pressure, or by more sophisticated methods of direct processing of the oscillatory complexes.

The Ramsey patents devote considerable effort and disclosure to the rejection of artifact data and hence to the derivation of accurate blood pressure data. Indeed, as is apparent from FIG. 2 of the Ramsey patents, the most insubstantial portion of the measurement cycle (denominated "T3") is devoted to the execution of complex detection at the various pressure levels, measurement of signal peaks of true complexes, and processing those peaks in accordance with artifact rejection algorithms so in sequence to identify the pressure level at which the peaks are a relative maximum, that is, mean arterial pressure. As taught by the Ramsey patents, about thirty seconds of a total cycle of less than 40 seconds are devoted to these "T3" functions.

It is a primary object of the principles of the present invention to reduce the time required to proceed through the pressure decrementing steps, correspondingly to provide data more rapidly to the administering physician, and to increase patient comfort by speeding the deflation and decreasing the time at which arterial occlusion takes place. Corespondingly, such improvements in speed and comfort should be had without penalty to overall accuracy.

It is a subsidiary but related object to make such improvements to systems of the class described in the Ramsey patents, with but minimal hardware or software variation, thereby to provide data and performance which is consistent with the considerable mass of clinical data already available for such systems.

SUMMARY OF THE INVENTION

The principles of the present invention are premised on the proposition that full scale artifact rejection criteria should be applied at the beginning of each inflation—deflation cycle, but that after a predetermined succession of "true" complexes are identified, abbreviated artifact rejection criteria may be utilized. In particular, in accordance with the principles of the present invention, at early pressure decrements in the cycle, as per the teachings of the Ramsey patents at least two complexes per level are detected, their respective peaks are identified and compared with one another, and they are identified as "true" complexes if they are within a specified range of one another, for example 20%. In accordance with the principles of the present invention, if such true complexes are identified in this fashion for a certain number (e.g. 2 or 3) of successive levels, abbreviated criteria may be adopted, for example at subsequent decrement levels simply detecting a single complex, and identifying its peak as a "true" peak at that level simply if it is in relative time correspondence with previously detected complexes (i.e. within a "heart rate window"), and is within a specified amplitude range of a next previous peak (e.g. 50%). If these heart rate timing and amplitude criteria are not met, however, the system automatically reverts to the more detailed artifact rejection schemes, involving detection of multiple complexes at each pressure decrement level. As desired, the principles of the present invention may be applied together with other, more sophisticated artifact rejection methods as taught by Ramsey, for example the time rate of change criterion which in accordance with the Ramsey patents is applicable simultaneously with use of amplitude criteria as described above. Through application of the principles of the present invention, the cycle time may be reduced by the amount of time saved at each level at which one, rather than more than one, complex is determined prior to the next decrementation of cuff pressure. In practical systems, this time savings may be on the order of 5–10 seconds per cycle, which otherwise may have been in the range of 25–30 seconds.

BEST MODE FOR CARRYING OUT THE INVENTION

U.S. Pat. Nos. 4,360,029 and 4,349,034 to M. Ramsey III are incorporated by reference herein. In particular, the principles of the present invention may be incorporated with relatively minimum difficulty into systems and methods set forth in the Ramsey patents.

It is worthy of note that the Ramsey patents are configured in terms of apparatus embodiments, the functional blocks of which are each set forth in extensive detail, including function. It is to be understood that the disclosure of the Ramsey patents is sufficiently precise to be made and used without undue experimentation either in the form of a dedicated hard wired system, in the form of a suitably programmed microprocessor based system, or as a hybrid of both. Indeed, widespread availability of relatively low-cost microprocessor and associated memory apparatus has made that embodiment the implementation of choice. Further, as of the date of filing hereof, software implementation is the best mode contemplated by the inventors hereof. If is to be understood, however, that such implementation should no way be taken as limiting, and in the very near future, the availability of low-cost specially designed very large scale integration (VLSI) may once more make hard wired systems the embodiment of choice. For emphasis, it deserves restatement that the disclosures set forth herein, together with those in the referenced Ramsey patents, are sufficient under the statute for either mode of embodiment.

Figure 1:
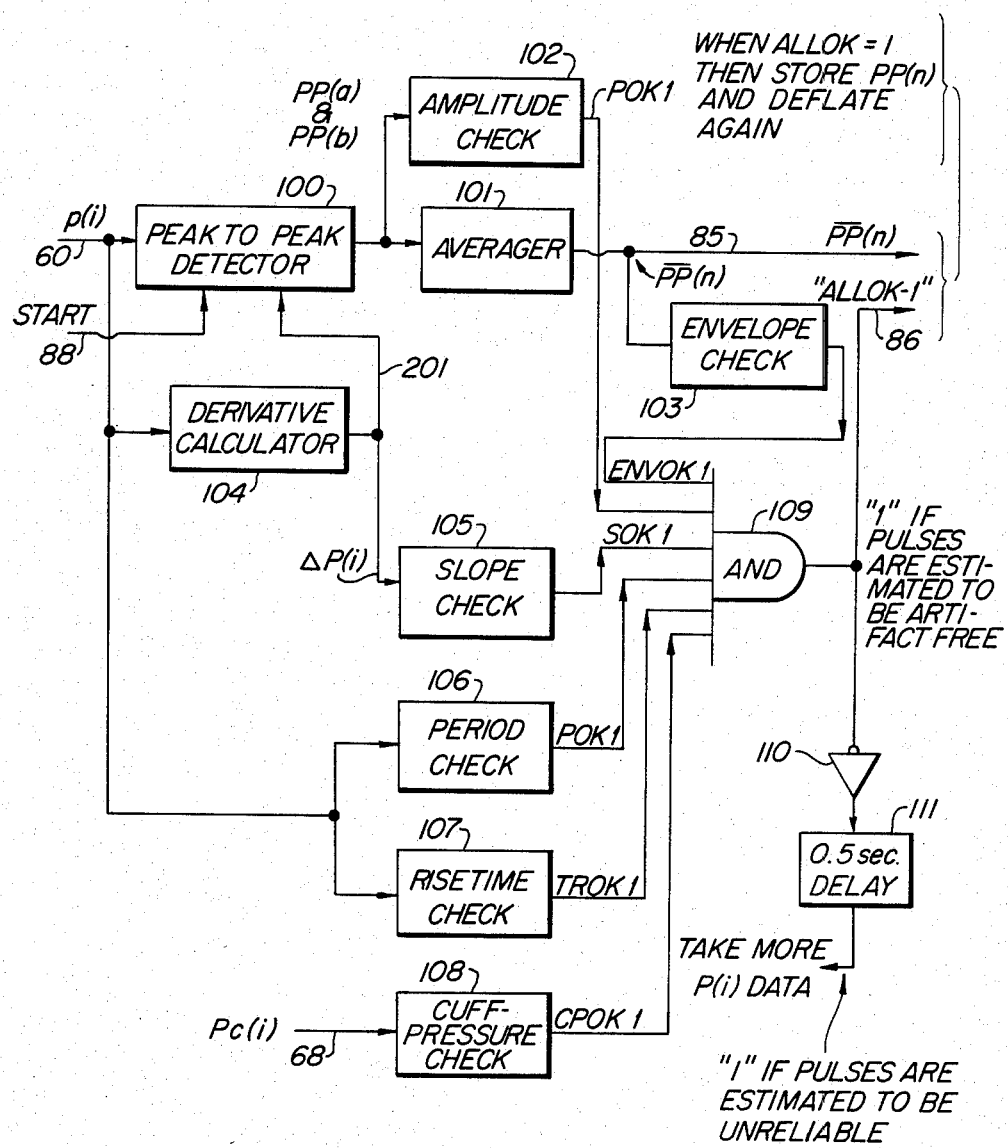
FIG. 1 replicates FIG. 6 of the cited Ramsey patents, which in turn discloses a block diagram of the peak-to-peak calculator and artifact rejection circuits of those patents.

Reference is first had to FIG. 1 (FIG. 6 of the Ramsey patents), which describes a relevant subsystem of the overall system and which is described in considerable detail in Cols. 8–10 of the Ramsey patent. In turn, numerous functional blocks of the subsystem of FIG. 1 are configured disclosed in greater detail in the Ramsey patents. It is to be noted that even in accrdance with the principles of the present invention, at the initiation of each measurement cycle, the self-same procedures as taught by Ramsey may be executed, until a certain number of true complexes have been identified (e.g. at 2 or 3 successive decrement levels), whereupon the more simplified, abbreviated artifact rejection criteria of the present invention are employed. Thus, in accordance with the principles of the present invention, the cuff is applied to the patient and inflated to a predetermined start level, and at each such level the heart pulse signal $p(i)$ is calculated and delivered to a peak-to-peak detector. The peak-to-peak detector 100 operates on the envelope of the oscillatory complex, and at each such cuff pressure level, respective first, PP(a), and second, PP(b) peaks are detected, and are coupled to an amplitude check circuit 102. The amplitude check circuit 102 determines whether the successive such peaks are within a certain range of one another, for example within 20% of one another. If they are, the complexes are designated as being "true" complexes, the amplitude check is satisfactory, and a logical 1 output signal is generated. If not, a logical 0 output signal is generated. It will be appreciated that the amplitude check circuit 102 is effective to detect pressure artifacts such as accidental striking of the cuff in synchronism with arterial pulses.

The purpose of the 20% tolerance requirement is to reject those beats which are widely variable in amplitude from beat to beat such as could be caused by premature ventricular contractions. Not only does this eliminate the acceptance of variable data during heartbeat irregularities, but it is also quite useful for reducing the influence of pulsation artifacts caused by subject motion or outside interference such as physician bumping against the cuff as could occur in an operation.

It will be noted that simultaneously a slope check 105, a period check 106, and a rise time check 107 are being conducted. These optional further criteria, together with the envelope check 103, provide a joint and accurate artifact rejection scheme. In all events, however, at this stage of the processing, successive complexes are detected at each pressure level and the slope check, period check, rise time check, and the like are subservient to the basic amplitude discrimination from the amplitude check 102 and the envelope check 103. In accordance with the principles of the present invention, once these checks have "passed" for two or three successive pressure levels, as desired, it is not necessary to continue to require the redundant complex amplitude checks, but rather simply to utilize a decrement to decrement envelope check, together with a period check such as set forth in 106.

Figure 2:
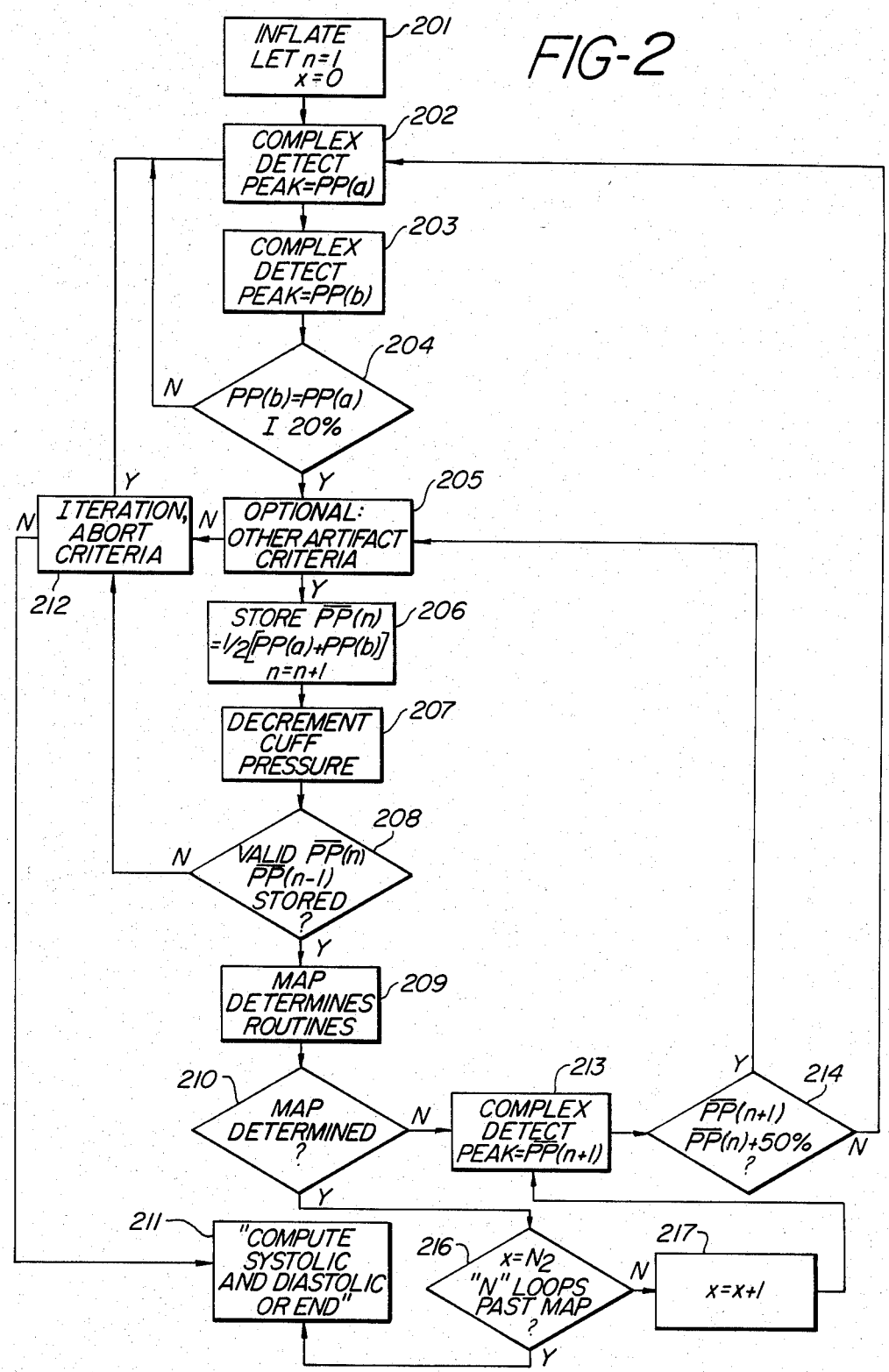
FIG. 2 shows in block diagramatic form a method embodying the principles of the present invention, the procedures therein being particularly amenable to software implementation.
Figure 3:
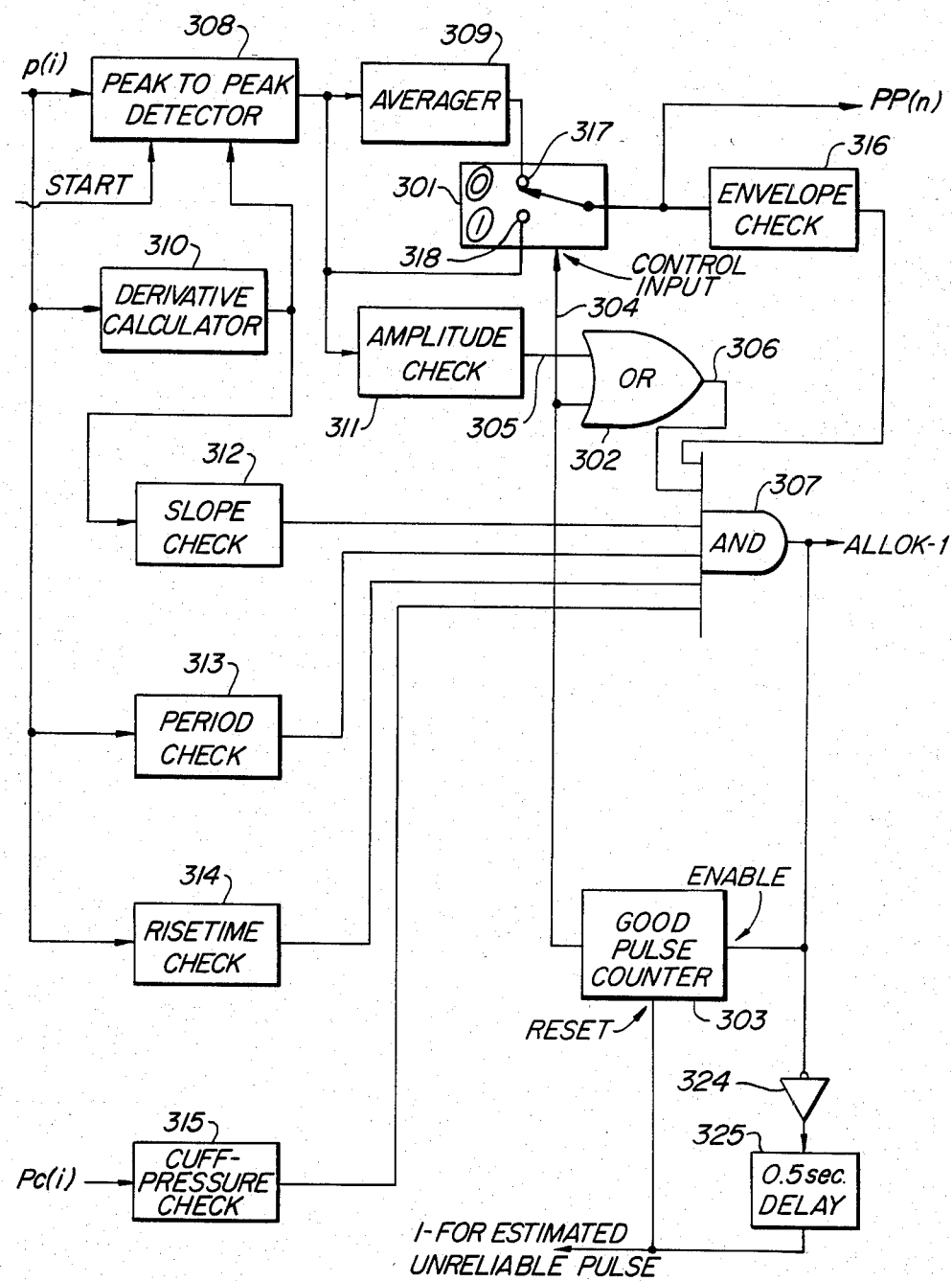
FIG. 3 shows an illustrative modification of the FIG. 1 apparatus in accordance with the principles of the present invention.

The operation of the principles of the present invention in conjunction with the apparatus of FIG. 6, as well as the balance of the apparatus of the referenced Ramsey patents, will be better appreciated upon consideration of FIG. 2. FIG. 2 will be recognized as a flow chart from which the principles of the present invention are to be executed, which flow chart may be taken directly to code, in the case of a software style system, or which may be implemented as shown in FIG. 3 as modifications to the hardwire system of FIG. 1. The procedures of FIG. 2 assume the rest of the system operating as described, and therefore simply highlight the modifications needed for incorporation of the principles of the present invention.

An initial inflate cuff step 201 assumes all of the preparatory T1 and T2 steps of the Ramsey patents, and the initiation of the T3 steps. Additionally, a cuff pressure level flag marker "n" is set at 1, and a post-man iteration marker "X" is set at 0. Thereupon, at 202 and 203, successive complexes are detected, and their peak levels are evaluated. In each case, a suitable procedure is disclosed in the Ramsey patents. Thereupon, also as disclosed in the Ramsey patents, the successive peaks are compared with one another, to determine whether the second varies by less than 20% from the first. If not, no "true" complex has been detected, and further data must be gathered. Assuming the peaks do compare favorably, that is that the amplitude criteria are met, the "yes" branch is taken from comparison step 204, and, as desired, other artifact criteria may be employed, as represented by step 205. These will be recognized as including, as desired, one or more of a slope check, period check, rise time check, envelope check, and the like. Assuming these artifact criteria are not met, the "fail" step is taken, to recycle and search for correct data in similar instance to the "no" exit from compare step 204. Suitable iteration abort criteria are applied at 212 to insure that the system does not get stuck in an endless loop.

Assuming that the other artifact criteria at 205 are met, that is that all artifact criteria are met, the "pass" branch is followed from step 205 to step 206, at which the associated of value PP(n) is calculated stored, that being recognized as the average of PP(a) and PP(b), pursuant to the teachings of the Ramsey patents. The flag marker n is incremented by 1, and at 207 the cuff pressure is decremented.

To this point, the operation has been more or less standard in the fashion of the Ramsey patents. At the next step, however, comparison 208, the procedure determines how many prior pressure decrement levels in succession have yielded true complexes and stored valid average peaks. In the method shown, two such steps are adequate to follow the "yes" branch (and thereby to initiate the abbreviated procedures in accordance with the principles of the present invention), but it is understood that a different number of levels, for example three or more, may also be utilized. Assuming that two such values are not in storage, and that the principles of the present invention are not yet ripe for application, the "no" exit is followed from 208, and the whole cycle is to be repeated for the new pressure level subject always to the iteration abort criteria.

If the "yes" exit is followed from step 208, the operation at step 209 refers generally to the execution of those procedures necessary for evaluating mean arterial pressure. That is, the mean arterial pressure procedures are completed to determine the pressure at which the peaks are a relative maximum. Optionally, these may be executed exactly as set forth in the Ramsey patent. Other modes of doing so will of course be equally appropriate.

In any event, the next step, 210, determines whether mean arterial pressure has been evaluated. If so, the "yes" branch is followed. Assuming not, however, the "no" branch exits from step 210, and the principles of the present invention are called into play. As shown at step 213, a single complex detection and peak determination is conducted at the new level, but rather than the more complex averaging and comparison as shown at 204, the peak is assigned the PP(n+1) value. At 214, this value is compared with the average valid peak from the previous level, to determine whether or not the variation is within specific acceptable limits, in the example shown, 50%. If not, indicating that the principles of the present invention will not be acceptable to continue defining peaks, the "no" branch is followed, back up to the initiation of the entire process from step 202. If so, however, the "yes" branch is followed, back up to the optional "other artifact criteria" step at 205. For example, in preferred embodiments of the principles of the present invention, a period check will be adequate further criterion to distinguish the data from artifacts. Assuming all is well, the loop continues, and will continue to do so through steps 206, 207, 208, 209, 210, 213, 214 and so on, until mean arterial pressure has been determined at 210, whereupon the yes exit is followed.

Once mean arterial pressure is so determined, it is desirable to check a predetermined further number of levels in order to assist in the diastolic pressure evaluation. As earlier stated, the flag variable "X" was set in order to allow for this check. From the yes branch of decision box 210, the routine moves to another decision box 216, determining whether X equals N, the number of levels at which complexes are to be checked past means arterial pressure. If fewer than "N" loops have been accomplished (i.e. fewer than the predetermined number of levels past means have been investigated), the no branch is followed from steps 216, the "X" variable is incremented by one at 217, and the routine returns to steps 213 and 214 in order to provide the peak measurement functions for each such level. Once the "N" levels past means have been checked, the routine flows from decision box 216 via the yes branch, thereby to complete the routine. As shown at box 211, the actual systolic and diastolic computation routine may be conducted. In the unlikely event that means arterial pressure is the only data desired, the routine is at an end.

It will be appreciated from the foregoing that, in the case of software embodiments of the Ramsey methods, but minimal software changes in accordance with FIG. 2 will be required, and that such changes are well within the ability of those of ordinary skill. In the event, however, that one wishes to modify the hardwire version as shown in the Ramsey patent, recourse is had to FIG. 3 as follows. In particular, FIG. 3 is configured similarly to FIG. 1, except that a few additions have been provided in order to accommodate the principles of the present invention. These additions are represented by a switch 301, an or-gate 302, and a "good pulse counter" 303. Operation of these elements in conjunction with the rationale of the present invention as discussed with FIG. 2 will result in gainful operation of the principles of the present invention in hard wired form.

As in FIG. 1, signal flow at the input is provided in parallel fashion to a peak to peak detector 308, a derivative calculation 310, a period check element 313, and a rise time check 314. The latter three elements are coupled, as in the FIG. 1 embodiment and in the aforementioned Ramsey patent, to an and-gate 307. Another input to the and-gate 307 is from a slope check 312 via the derivative calculation 310, again in accordance with the prior art.

The signal from the peak to peak detector is coupled to an averager (e.g. integrator) 309, an amplitude check 311, and to one pole 318 of the bypass switch 301. The other pole 317 of the bypass switch 301 is coupled to the output of the averager 309. Therefore, depending upon the position of the switch 301 (under control of the "good pulse counter" 303) the envelope check circuit will receive either the output of the averager 309, or the peak signal directly from 308.

In the FIG. 3 embodiment, the peak signal from 308 through the amplitude check 311 is coupled directly to one input of the or-gate 302, the other input of which is the output of the good pulse counter 303. In turn, the envelope check signal 316 and the output 306 of the or-gate 302 are also coupled to the and-gate 307. It is the output of the and-gate 307 which enables the good pulse counter to generate a logical 1 at its output, and thence to control the bypass switch 301 as well as the or-gate 302. The counter 303 itself is a simple gated counter which, upon receipt of two successive logical 1's from the and-gate 307, generates a logical 1 at its output thereby both to energize the or-gate 302, and to switch the bypass switch 317 to defeat the amplitude test after two good pulses have been received. Similarly, a logical 1 from the counter 303, after two good pulses have been received, cause the bypass switch to be moved to the lower position 318 and thus also to bypass the averager 309.

In operation, at the initiation of each cycle the switch 301 is at the uppermost position 317, thereby including the averager 309 in the processing. The counter 303, having been reset automatically by the delay unit, has its output at a logical zero. Since the amplitude check 311 has not yet yielded any favorable indication, the output 306 of the or-gate 302 is also at a logical zero state, and the output of and-gate 307 is similarly at a logical zero. Incoming signals are therefore processed in the same fashion as in the FIG. 1 apparatus. At some point, however, all of the checks, including the peak to peak and envelope check, the amplitude check, the slope check, the period check, the rise time check, and the cuff pressure check are satisfied (i.e. all outputs are logical 1's, which are conveyed to inputs of the and-gate 307), and the system output as well as the input to the counter 303 goes to a logical 1. If and only if the next consecutive complex also satisfies all checks, and yet another logical 1 is presented thereby to the counter 303, the output of the counter 303 goes to a logical 1 and the switch 301 is moved to its bypass mode, that is closed to the lowermost terminal 318. For the next sequence of signals, so long as the various other checks are satisfied, the averaging routine will be obviated. When and if the balance of the checks are not satisfied, or in the alternative the passage of the delay at 325 (which upon operation of inverter 324 commences with the first such logical 1), straight detection is permitted.

It will be appreciated that, in accordance with the embodiment of FIG. 3, some or all of the various slope checks, period checks, rise time checks, and the like may either be dispensed with in accordance with the needs of the designer, or enhanced and made further complicated in accordance therewith. In either event, just as in the case of the prior art, those checks form different and sometimes useful artifact rejection criteria which may in some instances be useful in conjunction with the principles of the present invention, and in others may not. In either event, the principles of the present invention are deemed to have independent utility. Further, it will be appreciated that the principles of the present invention themselves are as characterized by the spirit and scope of the claims appended hereto, and that numerous alternative embodiments will occur to those of ordinary skill without departure from the spirit or scope of the principles of the present invention.

We claim:

1. In an automatic oscillometric blood pressure system measurement method utilizing successive decremental arterial counterpressures to measure blood pressure complexes through detection of counterpressure oscillation, an improved detection method comprising:
   (a) establishing a predetermined counterpressure above systolic pressure;
   (b) decrementing said counterpressure in predetermined decrements to different pressure levels, each such pressure level being maintained for at least a predetermined duration;
   (c) sensing more than one complex at a first predetermined number of pressure levels, and comparing successive complex peak amplitudes at each such level to detect onset of true blood pressure complexes; and
   (d) after said detection of true complexes at a predetermined number of successive such pressure levels, commencing sensing but one complex at each level.

2. A method as described in claim 1 wherein said step of sensing but one complex per level includes comparing each such complex at each such level with predetermined validity criteria based on immediately prior complexes.

3. A method as described in claim 2, wherein said validity criteria include amplitude criteria based on the amplitude of the peak height of previous complexes, and timing window criteria based on heart rate as determined from the rate of occurrence of previous complexes.

4. A method as described in claim 1, wherein counterpressure is established by inflation pressure of a cuff on the subject.

* * * * *

UNITED STATES PATENT AND TRADEMARK OFFICE
CERTIFICATE OF CORRECTION

PATENT NO. : 4,543,962

DATED : October 1, 1985

INVENTOR(S) : Richard Medero, Rush W. Hood, Howard P. Apple

It is certified that error appears in the above-identified patent and that said Letters Patent is hereby corrected as shown below:

Col. 8, lines 10-11 "system" should be deleted.

Signed and Sealed this

Eighth Day of April 1986

[SEAL]

Attest:

DONALD J. QUIGG

Attesting Officer

Commissioner of Patents and Trademarks